(12) United States Patent
Chung et al.

(10) Patent No.: US 12,380,554 B2
(45) Date of Patent: Aug. 5, 2025

(54) METHOD FOR DETECTING ABNORMAL FINDINGS AND GENERATING INTERPRETATION TEXT OF MEDICAL IMAGE

(71) Applicant: VUNO Inc., Seoul (KR)

(72) Inventors: Minki Chung, Seoul (KR); Beomhee Park, Seoul (KR); Seo Taek Kong, Yongin-si (KR); Younjoon Chung, Seoul (KR)

(73) Assignee: VUNO Inc., Seoul (KR)

( * ) Notice: Subject to any disclaimer, the term of this patent is extended or adjusted under 35 U.S.C. 154(b) by 430 days.

(21) Appl. No.: 17/471,001

(22) Filed: Sep. 9, 2021

(65) Prior Publication Data

US 2022/0084200 A1 Mar. 17, 2022

(30) Foreign Application Priority Data

Sep. 14, 2020 (KR) .......................... 10-2020-0117511

(51) Int. Cl.
| | | |
|---|---|---|
| *G06V 20/40* | (2022.01) | |
| *G06T 7/00* | (2017.01) | |
| *G16H 30/40* | (2018.01) | |
| *G16H 50/20* | (2018.01) | |
| *G16H 50/30* | (2018.01) | |

(52) U.S. Cl.
CPC ........... *G06T 7/0012* (2013.01); *G16H 30/40* (2018.01); *G16H 50/20* (2018.01); *G16H 50/30* (2018.01); *G06T 2207/30096* (2013.01)

(58) Field of Classification Search
USPC ...... 382/128–224; 600/300–550; 704/1–275; 706/1–62, 900–903
See application file for complete search history.

(56) References Cited

U.S. PATENT DOCUMENTS 10,290,097 B2   5/2019   Shin et al.
10,691,980 B1   6/2020   Guendel et al.
(Continued)

FOREIGN PATENT DOCUMENTS

CN   108615237 A   10/2018
JP   2015191286 A   11/2015
(Continued)

OTHER PUBLICATIONS

Jonathan David Bloom, Device for Measuring the Temperature Distribution in the Sole of the Foot; Nov. 4, 2016 (Year: 2016).*
(Continued)

*Primary Examiner* — Marcellus J Augustin
(74) *Attorney, Agent, or Firm* — Seed IP Law Group LLP

(57) ABSTRACT

According to an embodiment of the present disclosure, an image analysis method is disclosed. The image analysis method may include: receiving a body medical image; detecting one or more lesions from the received body medical image using a lesion detection model; generating anatomical location information for the one or more lesions using an anatomical analysis model, based on the received body medical image and the detection result for the one or more lesions; and generating a diagnosis result for the received body medical image, based on the anatomical location information for the one or more lesions.

15 Claims, 8 Drawing Sheets

(56) References Cited

U.S. PATENT DOCUMENTS

| | | | |
|---|---|---|---|
| 11,633,084 B2* | 4/2023 | Hirasawa | G06T 7/0012 |
| | | | 382/128 |
| 11,742,073 B2* | 8/2023 | Cheng | G06N 3/045 |
| | | | 382/132 |
| 2009/0252395 A1 | 10/2009 | Chan et al. | |
| 2014/0122515 A1 | 5/2014 | Lee et al. | |
| 2015/0230773 A1 | 8/2015 | Cho et al. | |
| 2016/0022238 A1* | 1/2016 | Park | A61B 6/5217 |
| | | | 600/407 |
| 2017/0206653 A1 | 7/2017 | Shin et al. | |
| 2022/0114801 A1* | 4/2022 | Xu | G06V 10/44 |

FOREIGN PATENT DOCUMENTS

| | | |
|---|---|---|
| JP | 2019532390 A | 11/2019 |
| JP | 2020060857 A | 4/2020 |
| KR | 10-2015-0098119 A | 8/2015 |
| KR | 10-2016-0012758 A | 2/2016 |
| KR | 10-2017-0047839 A | 5/2017 |
| KR | 10-2017-0086311 A | 7/2017 |
| KR | 10-1857624 B1 | 5/2018 |
| KR | 10-1941209 B1 | 4/2019 |
| KR | 10-2019-0090986 A | 8/2019 |
| KR | 10-2019-0105210 A | 9/2019 |
| WO | WO 2019208130 A1 | 10/2019 |

OTHER PUBLICATIONS

Taerum Torin; Automated Lesion Detection, Segmentation, and Longitudinal Identification; Dec. 6, 2018 (Year: 2018).*

Lee Gun Woo; Apparatus and Method for Diagnosis of Medical Image; Jun. 3, 2019 (Year: 2019).*

Chen, Yu-fei; A CT Image Classification Method of Liver Tumour Based on Three Decision; 2017 (Year: 2017).*

Hirakawa, Shinnosuke; Medical Document Display Control Device, Medical Document Display Control Method, and Medical Document Display Control Program; 2019 (Year: 2019).*

* cited by examiner

METHOD FOR DETECTING ABNORMAL FINDINGS AND GENERATING INTERPRETATION TEXT OF MEDICAL IMAGE

CROSS-REFERENCE TO RELATED APPLICATIONS

This application claims priority to and the benefit of Korean Patent Application No. 10-2020-0117511 filed in the Korean Intellectual Property Office on Sep. 14, 2020, the entire contents of which are incorporated herein by reference.

BACKGROUND

Technical Field

The present disclosure relates to a medical image processing method, and more particularly, to a method of detecting a lesion from a body medical image by using a neural network model and generating a readout.

Description of the Related Art

A medical imaging technology is a technology that allows people to understand physical states of various organs in the human body. The medical imaging technology in the related art includes digital radiographic image (X-ray), Computed Tomography (CT), Magnetic Resonance Imaging (MRI), and the like.

In a method of detecting abnormal findings of a patient by using the medical imaging technology in the related art, a reader directly reads a body image or body imaging of the patient and detects a lesion.

Korean Patent No. 10-1941209 discloses a system and a method of automatically diagnosing a disease based on artificial intelligence.

BRIEF SUMMARY

The inventors of the present disclosure have identified and appreciated that some approaches in the prior art has problems. For instance, the method of detecting abnormal findings of a patient by using the medical imaging technology in the related art has a problem in that the region of the image that is mainly viewed by the reader may be different. Further, there is a slight deviation in the reading result depending on the viewpoint of the reader, causing a problem in that a consistent and professional reading is impossible. In order to solve the problems in the related art as well as those technical problems identified by the inventors, the inventors have provided one or more embodiments associated with a reading technique capable of reading a medical image more professionally and consistently or a reading assisting technique capable of assisting to provide consistent reading.

One or more embodiments of the present disclosure provide a method of detecting abnormal findings in a body medical image and providing a readout which addresses one or more problems in the related art.

According to an embodiment for implementing the foregoing object, a method performed in one or more processors of a computer device is disclosed. The method may include: receiving a body medical image; detecting one or more lesions from the received body medical image using a lesion detection model; generating anatomical location information for the one or more lesions using an anatomical analysis model, based on the received body medical image and the detection result for the one or more lesions; and generating a diagnosis result for the received body medical image, based on the anatomical location information for the one or more lesions.

According to an embodiment for implementing the foregoing object, a method performed in one or more processors of a computer device is disclosed. The method may include: receiving a body medical image; detecting one or more lesions from the received body medical image using a lesion detection model; extracting a body region having anatomical significance from the received body medical image using an anatomical analysis model; generating anatomical location information for the one or more lesions by matching the detection result for the one or more lesions with the extracted body region; and generating a diagnosis result for the received body medical image, based on the anatomical location information for the one or more lesions.

In an alternative embodiment, the extracted body region may be divided into a plurality of sub regions, and the generating the anatomical location information for the one or more lesions may include: determining a location in which the one or more lesions exist in the divided sub regions by matching the detection result for the one or more lesions with the plurality of sub regions for the extracted body region; and generating the anatomical location information indicating that the one or more lesions exist in the determined location.

In the alternative embodiment, the detecting the one or more lesions from the received body medical image using the lesion detection model may include: determining type information of the one or more lesions included in the received body medical image; determining a confidence score corresponding to the determined type information of the one or more lesions; and generating contour information of the detected one or more lesions.

In the alternative embodiment, the generating the diagnosis result for the received body medical image, based on the anatomical location information for the one or more lesions may include: generating clinical information indicating clinical significance in a situation in which the one or more lesions are related to the anatomical location information; and generating a readout using a readout generation model, based on the generated clinical information.

In the alternative embodiment, the generating the diagnosis result for the received body medical image, based on the anatomical location information for the one or more lesions may further include: modifying the generated readout by reflecting a modification input of a user; and generating the diagnosis result for the received body medical image based on the modified readout.

In the alternative embodiment, the clinical information may include: an occurrence frequency of lesion for each of regions divided from the body region having the anatomical significance; and a degree of risk of lesion for each of the divided regions.

In the alternative embodiment, the generating the clinical information indicating the clinical significance in the situation in which the one or more lesions are related to the anatomical location information may include: changing a confidence score determined in the step of detecting the one or more lesions, based on the occurrence frequency of lesion for each of the divided regions which is obtained from clinical statistical information; and generating the clinical information, based on the changed confidence score and based on the degree of risk of lesion for each of the divided regions which is obtained from the clinical statistical information.

In the alternative embodiment, the method may further include generating a user interface including information on the diagnosis result, in which the user interface may include: a first area for displaying the detected one or more lesions on the received body medical image; a second area for displaying summary information about the detected one or more lesions; and a third area for displaying a readout corresponding to the diagnosis result.

In the alternative embodiment, the user interface may further include a notification area for providing additional information according to a degree of risk of lesion, in which whether to display the notification area may be determined based on at least one of the anatomical location information for the one or more lesions or a confidence score for the one or more lesions.

According to an embodiment of the present disclosure, a computer program including commands which are stored in a computer readable storage medium and cause a computer to perform following operations is disclosed. The operations may include: receiving a body medical image; detecting one or more lesions from the received body medical image using a lesion detection model; extracting a body region having anatomical significance from the received body medical image using an anatomical analysis model; generating anatomical location information for the one or more lesions by matching the detection result for the one or more lesions with the extracted body region; and generating a diagnosis result for the received body medical image, based on the anatomical location information for the one or more lesions.

According to an embodiment of the present disclosure, a server is disclosed. The server may include: a processor including one or more cores; a network unit receiving a body medical image; and a memory. The processor may detect one or more lesions from the received body medical image using a lesion detection model, extract a body region having anatomical significance from the received body medical image using an anatomical analysis model, generate anatomical location information for the one or more lesions by matching the detection result for the one or more lesions with the extracted body region, and generate a diagnosis result for the received body medical image, based on the anatomical location information for the one or more lesions.

According to an embodiment of the present disclosure, a method performed in a terminal is disclosed. The method may include: receive a diagnosis result including anatomical location information generated according to matching of one or more lesions detected from a body medical image and a body region having anatomical significance extracted from the body medical image from a server; providing a user interface (UI) including the received diagnosis result; and correcting the diagnosis result output on the user interface in response to a user input interacting with the user interface.

In an alternative embodiment, the user interface in the terminal may include: a first area for displaying the detected one or more lesions on the received body medical image; a second area for displaying summary information about the detected one or more lesions; and a third area for displaying a readout corresponding to the diagnosis result.

According to an embodiment of the present disclosure, a terminal is disclosed. The terminal may include: a processor including one or more cores; a memory; a network unit which receives a diagnosis result including anatomical location information generated according to matching of one or more lesions detected from a body medical image and a body region having anatomical significance extracted from the body medical image from a server; and an output unit which provides a user interface (UI) including the received diagnosis result, and responds to detection of a user input interacting with the user interface and displays a diagnosis result corrected in response to the user input on the user interface.

The present disclosure may detect abnormal findings in a body medical image and provide a diagnosis result.

DETAILED DESCRIPTION

Figure 1:
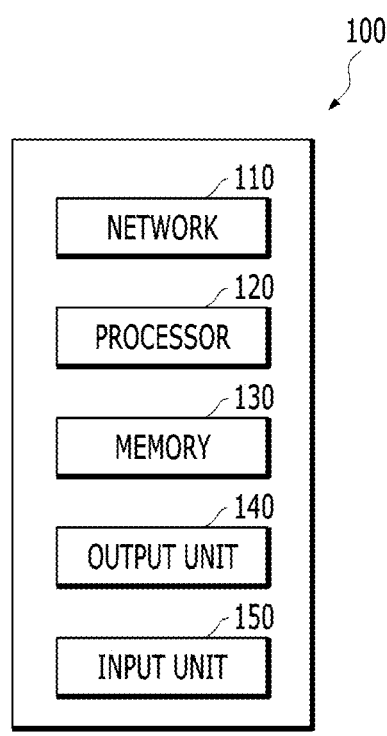
FIG. 1 is a block diagram illustrating a computing device according to an embodiment of the present disclosure.

Various embodiments are described with reference to the drawings. In the present specification, various descriptions are presented for understanding the present disclosure. However, it is obvious that the embodiments may be carried out even without a particular description.

Terms, "component," "module," "system," and the like used in the present specification indicate a computer-related entity, hardware, firmware, software, a combination of software and hardware, or execution of software. For example, a component may be a procedure executed in a processor, a processor, an object, an execution thread, a program, and/or a computer, but is not limited thereto. For example, both an application executed in a computing device and a computing device may be components. One or more components may reside within a processor and/or an execution thread. One component may be localized within one computer. One component may be distributed between two or more computers. Further, the components may be executed by various computer readable media having various data structures stored therein. For example, components may communicate through local and/or remote processing according to a signal (for example, data transmitted to another system through a network, such as the Internet, through data and/or a signal from one component interacting with another component in a local system and a distributed system) having one or more data packets.

A term "or" intends to mean comprehensive "or" not exclusive "or." That is, unless otherwise specified or when it is unclear in context, "X uses A or B" intends to mean one of the natural comprehensive substitutions. That is, when X uses A, X uses B, or X uses both A and B, "X uses A or B" may be applied to any one among the cases. Further, a term "and/or" used in the present specification shall be understood to designate and include all of the possible combinations of one or more items among the listed relevant items.

It should be understood that a term "include" and/or "including" means that a corresponding characteristic and/or a constituent element exists. Further, a term "include" and/or "including" means that a corresponding characteristic and/or a constituent element exists, but it shall be understood that the existence or an addition of one or more other characteristics, constituent elements, and/or a group thereof is not excluded. Further, unless otherwise specified or when it is unclear in context that a single form is indicated in context, the singular shall be construed to generally mean "one or more" in the present specification and the claims.

The term "at least one of A and B" should be interpreted to mean "the case including only A," "the case including only B," and "the case where A and B are combined."

The term "unit" may include any electrical circuitry, features, components, an assembly of electronic components or the like. That is, "unit" may include any processor-based or microprocessor-based system including systems using microcontrollers, integrated circuit, chip, microchip, reduced instruction set computers (RISC), application specific integrated circuits (ASICs), field-programmable gate arrays (FPGAs), graphical processing units (GPUs), logic circuits, and any other circuit or processor capable of executing the various operations and functions described herein. The above examples are examples only, and are thus not intended to limit in any way the definition or meaning of the term "unit."

In some embodiments, the various units described herein may be included in or otherwise implemented by processing circuitry such as a microprocessor, microcontroller, or the like.

Those skilled in the art shall recognize that the various illustrative logical blocks, configurations, modules, circuits, means, logic, and algorithm operations described in relation to the embodiments additionally disclosed herein may be implemented by electronic hardware, computer software, or in a combination of electronic hardware and computer software. In order to clearly exemplify interchangeability of hardware and software, the various illustrative components, blocks, configurations, means, logic, modules, circuits, and operations have been generally described above in the functional aspects thereof. Whether the functionality is implemented as hardware or software depends on a specific application or design restraints given to the general system. Those skilled in the art may implement the functionality described by various methods for each of the specific applications. However, it shall not be construed that the determinations of the implementation deviate from the range of the contents of the present disclosure.

The description about the presented embodiments is provided so as for those skilled in the art to use or carry out the present disclosure. Various modifications of the embodiments will be apparent to those skilled in the art. General principles defined herein may be applied to other embodiments without departing from the scope of the present disclosure. Therefore, the present disclosure is not limited to the embodiments presented herein. The present disclosure shall be interpreted within the broadest meaning range consistent to the principles and new characteristics presented herein.

In an embodiment of the present disclosure, a server may also include other configurations for performing a server environment. The server may include all of the predetermined types of devices. The server is a digital device, and may be a digital device, such as a laptop computer, a notebook computer, a desk top computer, a web pad, a mobile phone, which is equipped with a processor, includes a memory, and has computing capability. The server may be a web server processing the service. The kind of foregoing server is merely an example, and the present disclosure is not limited thereto.

In the present specification, a neural network, an artificial neural network, and a network function may often be interchangeably used.

The term "image" or "image data" used throughout the detailed description and the claims of the present disclosure refers to multidimensional data composed of discrete image elements (for example, pixels in a 2-dimensional image), and in other words, is the term referring to a target visible to the eye (displayed on a video screen) or a digital representation of the target (for example, a file corresponding to a pixel output of a CT or MRI detector).

For example, "image" or "imaging" may be a medical image of a subject collected by Computed Tomography (CT), Magnetic Resonance Imaging (MRI), fundus image, ultrasonic rays, or other predetermined medical imaging systems publicly known in the art of the present disclosure. The image is not necessarily provided in a medical context, but may also be provided in a non-medical context, such as X-ray imaging for security screening.

Throughout the detailed description and the claims of the present disclosure, the "Digital Imaging and Communications in Medicine (DICOM)" standard is a term collectively referring to various standards used in digital imaging expression and communication in medical devices, and the DICOM standard is published by the allied committee formed by the American College of Radiology (ACR) and American National Electrical Manufacturers Associations (NEMA).

Throughout the detailed description and the claims of the present disclosure, a "Picture Archiving and Communication System (PACS)" is a term that refers to a system that stores, processes, and transmits images in accordance with the DICOM standard, and medical images obtained by using digital medical imaging equipment, such as X-ray, CT, and MRI, may be stored in the DICOM format and transmitted to terminals inside and outside a hospital through a network, and a reading result and a medical record may be added to the medical image.

A computing device 100 according to an embodiment of the present disclosure may include a processor 120, a network unit 110, a memory 130, an output unit 140, and an input unit 150.

The configuration of a computing device 100 illustrated in FIG. 1 is merely a simplified example. In the embodiment of the present disclosure, the computing device 100 may include other configurations for performing a computing environment of the computing device 100, and only some of the disclosed configurations may also configure the computing device 100.

In the present disclosure, the computing device 100 may mean a predetermined type of user terminal or a predetermined type of server. The foregoing components of the computing device 100 are illustrative, and some may be excluded or additional components may be included. For example, when the computing device 100 means a server, the output unit 140 and the input unit 150 of the computing device 100 may be excluded. When the computing device 100 includes a terminal, the output unit 140 and the input unit 150 may be included in the range of the terminal.

The processor 120 may be formed of one or more cores, and may include a processor, such as a central processing unit (CPU), a general purpose graphics processing unit (GPGPU), and a tensor processing unit (TPU) of the computing device, for performing a data analysis and deep learning. The processor 120 may read a computer program stored in the memory and perform data processing for machine learning according to the embodiment of the present disclosure. According to the embodiment of the present disclosure, the processor 120 may perform calculation for training a neural network. The processor 120 may perform a calculation, such as processing of input data for training in Deep Learning (DN), extraction of a feature from input data, an error calculation, and updating of a weight of the neural network by using backpropagation, for training the neural network. At least one of the CPU, GPGPU, and TPU of the processor 120 may process training of a network function. For example, the CPU and the GPGPU may process training of the network function and data classification by using a network function together. Further, in the embodiment of the present disclosure, the training of the network function and the data classification by using a network function may be processed by using the processors of the plurality of computing devices together. Further, the computer program executed in the computing device according to the embodiment of the present disclosure may be a CPU, GPGPU, or TPU executable program.

According to the embodiment of the present disclosure, the memory 130 may store a predetermined type of information generated or determined by the processor 120 and a predetermined type of information received by a network unit.

According to the embodiment of the present disclosure, the memory 130 may include at least one type of storage medium among a flash memory type, a hard disk type, a multimedia card micro type, a card type of memory (for example, an SD or XD memory), a Random Access Memory (RAM), a Static Random Access Memory (SRAM), a Read-Only Memory (ROM), an Electrically Erasable Programmable Read-Only Memory (EEPROM), a Programmable Read-Only Memory (PROM), a magnetic memory, a magnetic disk, and an optical disk. The computing device 100 may also be operated in relation to web storage performing a storage function of the memory 130 on the Internet. The description of the foregoing memory is merely illustrative, and the present disclosure is not limited thereto.

The network unit in the present disclosure may be configured regardless of its communication mode, such as a wired mode and a wireless mode, and may be configured of various communication networks, such as a Personal Area Network (PAN) and a Wide Area Network (WAN). Further, the network may be the publicly known World Wide Web (WWW), and may also use a wireless transmission technology used in PAN, such as Infrared Data Association (IrDA) or Bluetooth.

According to the embodiment of the present disclosure, the server may transmit a diagnosis result including the anatomical location information generated according to the matching of the one or more lesions detected from the body medical image and the body region having the anatomical significance extracted from the body medical image to the terminal through the network unit 110.

According to the embodiment of the present disclosure, the terminal may receive the diagnosis result including the anatomical location information generated according to the matching of the one or more lesions detected from the body medical image and the body region having the anatomical significance extracted from the body medical image from the server through the network unit 110.

The technologies described in the present specification may be used in other networks, as well as the foregoing networks.

The output unit 140 according to the embodiment of the present disclosure may display a User Interface (UI) for providing a diagnosis result for the body medical image. The output unit 140 may display the user interface of the terminal illustrated in FIG. 5. The user interfaces illustrated in the drawing and described above are merely illustrative, and the present disclosure is not limited thereto.

The output unit 140 according to the embodiment of the present disclosure may output the predetermined form of information generated or determined by the processor 120 and the predetermined form of information received by the network unit 110.

In the embodiment of the present disclosure, the output unit 140 may include at least one of a Liquid Crystal Display (LCD), a Thin Film Transistor Liquid Crystal Display (TFT LCD), an Organic Light Emitting Diode (OLED), a flexible display, and a 3D display. Among them, some display modules may be configured as a transparent type or a light transmission type so that the outside can be seen through the display modules. This may be referred to as a transparent display module, and a representative example of the transparent display module includes a Transparent OLED (TOLED).

According to the embodiment of the present disclosure, the output unit 140 of the terminal may output the diagnosis result received from the server on the user interface. Further, the output unit 140 of the terminal may also correct and display the diagnosis result output on the user interface in response to the detection of the user input that interacts with the user interface.

A user input may be received through the input unit 150 according to the embodiment of the present disclosure.

The input unit 150 according to the embodiment of the present disclosure may be provided with keys and/or buttons, or physical keys and/or buttons on the user interface for receiving the user input. A computer program for controlling a display according to the embodiments of the present disclosure may be executed according to the user input through the input unit 150.

The input unit 150 according to the embodiments of the present disclosure may receive a signal by detecting a button manipulation or a touch input of a user or receive a voice or an operation of a user and the like through a camera or a microphone and convert the received signal, voice, or operation to an input signal. To this end, speech recognition technology or motion recognition technology may be used.

The input unit 150 according to the embodiments of the present disclosure may also be implemented as external input equipment connected with the computing device 100. For example, the input equipment may be at least one of a touch pad, a touch pen, a keyboard, and a mouse for receiving a user input, but this is merely an example, and the present disclosure is not limited thereto.

The input unit 150 according to the embodiments of the present disclosure may recognize a touch input of a user. The input unit 150 according to the embodiments of the present disclosure may have the same configuration as that of the output unit 140. The input unit 150 may be formed of a touch screen implemented so as to receive a selection input of a user. In the touch screen, any one of a contact type capacitance method, an infrared light sensing method, a Surface Ultrasonic Wave (SAW) method, a piezoelectric method, and a resistive film method may be used. The detailed description for the foregoing touch screen is merely illustrative according to the embodiments of the present disclosure, and various touch screen panels may be applied to the computing device 100. The input unit 150 formed of a touch screen may include a touch sensor. The touch sensor may be configured to convert a change in pressure applied to a specific region of the input unit 150 or electrostatic capacity generated in a specific region of the input unit 150 into an electric input signal. The touch sensor may be configured so as to detect pressure of a touch, as well as a location and an area of a touch. When a touch input is made to the touch sensor, a signal(s) corresponding to the touch input is transmitted to a touch controller. The touch controller processes the signal(s) and then transmits data corresponding to the signal(s) to the processor 120. Accordingly, the processor 120 may recognize a touched area of the input unit 150 and the like.

The server performing an operation of providing a user interface for providing a diagnosis result for a body medical image to a user terminal according to the embodiment of the present disclosure may include a network unit, a processor, and a memory.

The server may generate the user interface according to the embodiments of the present disclosure. The server may be a computing system which provides a client (for example, a user terminal) with information through a network. The server may transmit the generated user interface to the user terminal. In this case, the user terminal may be a predetermined form of computing device capable of accessing the server. The processor of the server may transmit the user interface to the user terminal through the network unit. The server according to the embodiments of the present disclosure may be, for example, a cloud server. The server may be a web server or a cloud server that processes services. The kind of foregoing server is merely an example, and the present disclosure is not limited thereto.

Each of the network unit, the processor, and the memory included in the server according to the embodiments of the present disclosure may perform the same roles as those of the network unit 110, the processor 120, and the memory 130 included in the computing device 100 or be identically configured to the network unit 110, the processor 120, and the memory 130 included in the computing device 100.

Figure 5:
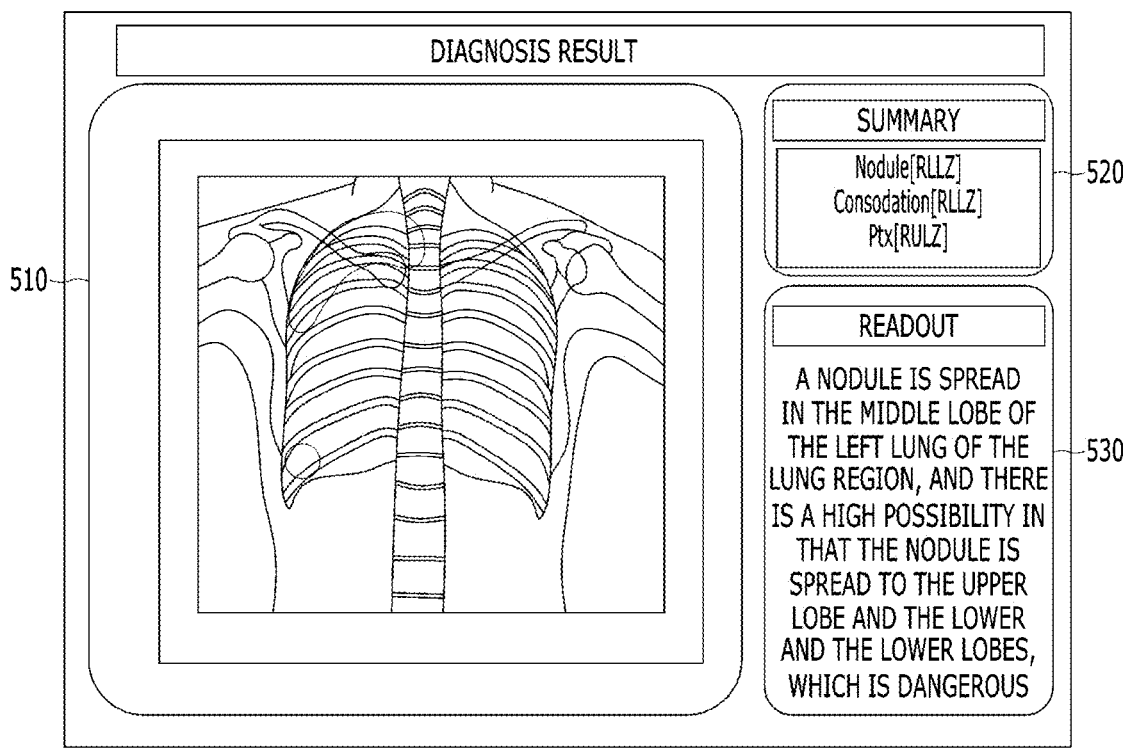
FIG. 5 is a diagram illustrating a user interface according to the embodiment of the present disclosure.

The user terminal may provide or display the user interface which is provided for providing the diagnosis result for the body medical image from the server. The user terminal may include a network unit, a processor, a memory, an output unit, and an input unit. Each of the network unit, the processor, the memory and the output unit of the user terminal may perform the same or similar operation as those of each of the network unit 110, the processor 120, the memory 130, the output unit 140, and the input unit 150 included in the computing device 100. For example, the user interface may be displayed through the output unit of the user terminal. For example, the user interface may be displayed as illustrated in FIG. 5.

Figure 2:
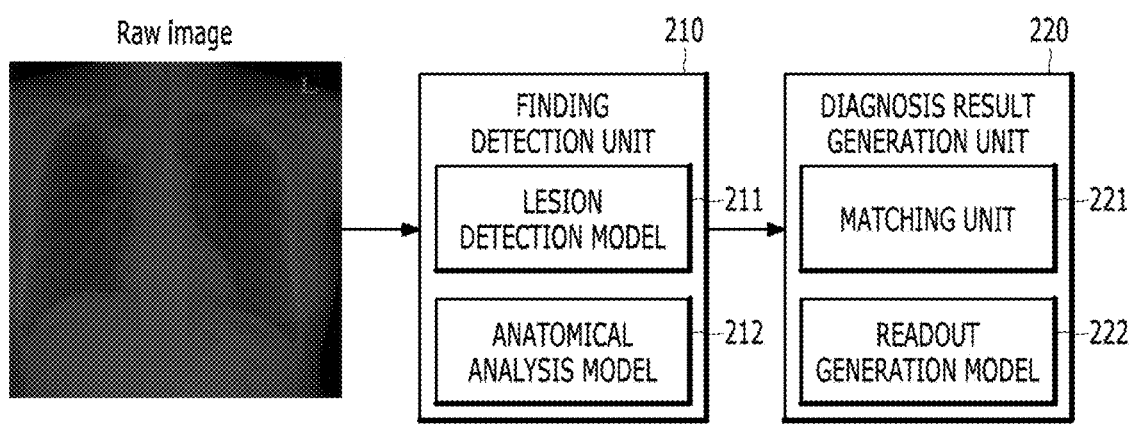
FIG. 2 is a block diagram illustrating an operation flow of a computing device 100 according to an embodiment of the present disclosure.

FIG. 2 is a block diagram illustrating an operation flow of the computing device 100 according to an embodiment of the present disclosure.

The configuration of the operation flow diagram of the computing device 100 illustrated in FIG. 2 is merely a simplified example. In the embodiment of the present disclosure, the operation flow diagram may include other configurations for performing a computing environment of the computing device 100, and some of the disclosed configurations may also configure the operation flow diagram.

The processor 120 according to the present disclosure may generate a diagnosis result determined to correspond to the body medical image and a readout corresponding to the diagnosis result from the body medical image by executing a computer program stored in a computer readable storage medium. To this end, the processor 120 may receive a body medical image, and detect one or more lesions from the body medical image received through a lesion detection model 211 of a finding detection unit 210. Further, the processor 120 may extract a body region having an anatomical significance from the received body medical image by using an anatomical analysis model 212. The processor 120 may generate anatomical location information for the one or more lesions by matching a detection result for the one or more lesions and the extracted body region through a matching unit 221 of a diagnosis result generation unit 220. Further, the processor 120 may generate a diagnosis result for the received body medical image based on the anatomical location information for the one or detected more lesions by using a readout generation model 222 of the diagnosis result generation unit 220.

In an additional embodiment of the present disclosure, the processor 120 may also generate anatomical location information for the one or more lesions by using an anatomical analysis model based on the received body medical image and a detection result of the one or more lesions.

In the present disclosure, the body medical image may be an image of a predetermined body region for generating information on the type of lesion and an anatomical location of the lesion in order to generate findings for the lesion. The body region may mean a system of the body in a broad sense, and may mean each body organ. The example of the body region is merely illustrative, and the present disclosure is not limited thereto.

The processor 120 according to the present disclosure may detect one or more lesions from the received body medical image by using the lesion detection model 211 of the finding detection unit 210. The processor 120 may determine type information of the one or more lesions included in the received body medical image by using the lesion detection model 211 of the finding detection unit 210. In particular, the processor 120 may determine the type of lesion for one or more lesions through a different modelling method for each lesion. For example, the type of lesion may include pleural effusion, pneumothorax, consolidation, interstitial opacity, and nodule, and the type of lesion may be determined based on an individual characteristics of lesions. Further, a size of lesion for each lesion of which the type is determined may be determined. A size is a diameter or an area, and may be digitized and expressed quantitatively.

The processor 120 may determine a confidence score corresponding to information on the determined type of one or more lesions. For example, the processor 120 may detect two lesions from the chest X-ray image through the lesion detection model 211 and determine pleural effusion and interstitial opacity for the lesions, respectively. In this case, in determining each lesion, it is possible to calculate a confidence score of the determination on each lesion, and the confidence scores of the lesions may be calculated as 80% and 40%, respectively. Accordingly, the probabilities of the pleural effusion and the interstitial opacity, which are the lesions determined by the processor 120, may be estimated to be 80% and 40%, respectively. The example of the confidence score of the lesion is merely illustrative, and the expression method of the confidence score may include a quantitative expression method (for example, a digitized value) or a qualitative expression method (for example, an opinion or description of a confidence score).

In an additional embodiment, the processor 120 may generate outline information of the one or more determined lesions.

Figure 3:
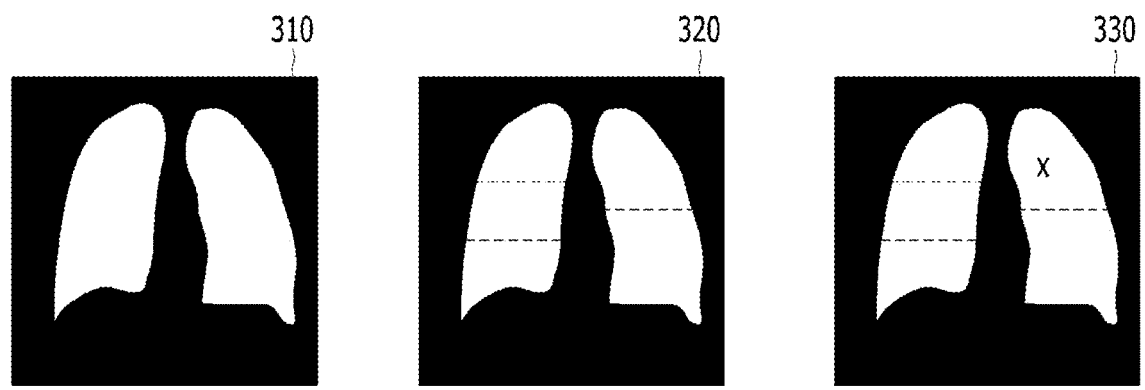
FIG. 3 is a diagram illustrating anatomical location information about a lesion in the body medical image according to the embodiment of the present disclosure.

FIG. 3 is a diagram illustrating anatomical location information about a lesion in the body medical image according to the embodiment of the present disclosure.

The processor 120 according to the present disclosure may extract a body region having an anatomical significance from the received body medical image by using the anatomical analysis model 212 of the finding detection unit 210. The processor 120 may extract a body region having an anatomical significance from the received body medical image by using a body region detection model that is a sub set of the anatomical analysis model 212. Herein, the anatomical significance may be a body organ that is likely to be the point of occurrence of one or more lesions or a body organ that may be the target of the detection of one or more lesions. For example, the processor 120 may extract a lung region 310 (for example, a whole region of the lung) in the chest X-ray image in which the interstitial opacity is likely to occur. The example of extracting the body part from the body medical image is merely illustrative, and the present disclosure is not limited thereto.

The processor 120 may divide the extracted body region into a plurality of sub regions by using the anatomical analysis model 212. Herein, the reference for dividing the body region into the plurality of sub regions may include area information derived from the extracted body region or inherent characteristic information of the body region. For example, the processor 120 may generate a lung region 320 by dividing the left lung into two upper and lower lobes and the right lung into three upper, middle, and lower lobes based on the area of the lung region 310 extracted from the chest X-ray image through the anatomical analysis model through the anatomical analysis model 212, or extract a heart region from a CT image and generate heart sub regions obtained by dividing the heart region into left ventricle, left atrium, right ventricle, and right atrium based on inherent characteristic information of the heart region. The example of dividing the body region is merely illustrative, and the present disclosure is not limited thereto.

The processor 120 may generate anatomical location information for the one or more lesions by matching a detection result of the one or more lesions and the extracted body region. In an additional embodiment, the processor 120 may also generate anatomical location information for the one or more detected lesions based on the received body medical image and the detection result for the one or more detected lesions by using the anatomical analysis model.

In particular, the processor 120 may determine a location, at which one or more lesions exist, in the divided sub regions. The processor 120 may generate anatomical location information that is information on the point in the divided sub region at which the one or more detected lesions exist. For example, the processor 120 may extract the lung region 310 from the chest X-ray image, generate the divided lung region 320 based on the area of the lung region 310, and match one lesion detected from the chest X-ray image and the divided lung region 320 to generate anatomical location information. The example of generating the anatomical location information is merely illustrative, and the present disclosure is not limited thereto.

In the embodiment of the present disclosure, the anatomical analysis model 212 may match the detected lesion and the sub regions of the body region by using a predetermined image processing method. For example, the detected lesion and the sub region of the body region may be matched by a method of matching the location information (for example, a coordinate value) about the detected lesion and the location information (for example, a coordinate value) for the sub region of the body region. In another embodiment, the anatomical analysis model 212 may match the detected lesion and the sub regions of the body region by using a deep neural network. The deep neural network will be described below.

As the embodiment of the present disclosure, the anatomical location information about the one or more detected lesions may be generated by the matching unit 221 of the diagnosis result generation unit 220 of the computing device 100. In particular, the processor 120 may receive a body medical image. The processor 120 may detect one or more lesions from the received body medical image by using the lesion detection model 211. Further, the processor 120 may extract a body region having an anatomical significance from the received body medical image by using the anatomical analysis model 212. The body region may be divided into a plurality of sub regions through the anatomical analysis model. Then, the processor 120 may generate anatomical location information for the one or more detected lesions through the matching unit 221 of the diagnosis result generation unit 220. In particular, the processor 120 may determine a location, at which the one or more lesions exist, in the divided sub regions by matching the detection result for the one or more detected lesions and the plurality of sub regions for the extracted body region. Further, the processor 120 may generate anatomical location information indicating that one or more lesions exist at the location determined through the matching unit 221 of the diagnosis result generation unit 220.

In the embodiment of the present disclosure, the matching unit 221 may match the detected lesion and the sub regions of the body region by using a predetermined image processing method. In another embodiment of the present disclosure, the matching unit 221 may match the detected lesion and the sub regions of the body region by using a deep neural network. The deep neural network will be described below.

Figure 4:
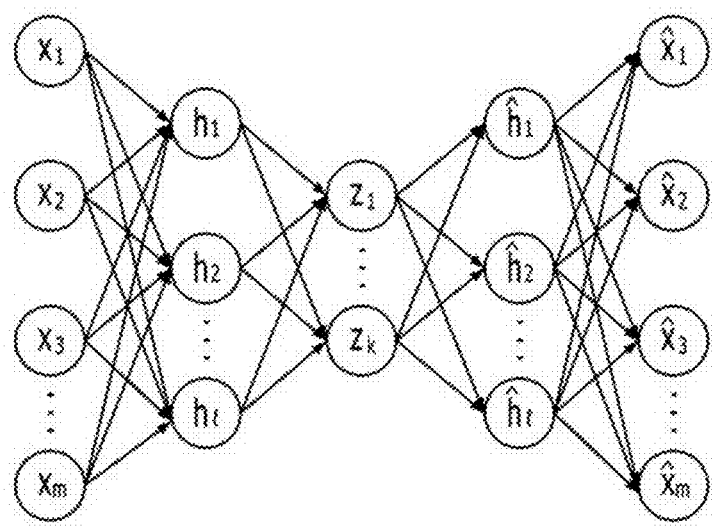
FIG. 4 is a schematic diagram illustrating a network function according to the embodiment of the present disclosure.

FIG. 4 is a schematic diagram illustrating a network function according to the embodiment of the present disclosure.

Throughout the present specification, a computation model, the neural network, a network function, and the neural network may be used as the same meaning. The neural network may be generally constituted by an aggregate of calculation units which are mutually connected to each other, which may be called nodes. The nodes may also be called neurons. The neural network is configured to include one or more nodes. The nodes (alternatively, neurons) constituting the neural networks may be connected to each other by one or more links.

In the neural network, one or more nodes connected through the link may relatively form the relationship between an input node and an output node. Concepts of the input node and the output node are relative and a predetermined (or selected) node which has the output node relationship with respect to one node may have the input node relationship in the relationship with another node and vice versa. As described above, the relationship of the input node to the output node may be generated based on the link. One or more output nodes may be connected to one input node through the link and vice versa.

In the relationship of the input node and the output node connected through one link, a value of the output node may be determined based on data input in the input node. Here, a node connecting the input node and the output node to each other may have a weight. The weight may be variable and the weight is variable by a user or an algorithm in order for the neural network to perform a desired (or selected) function. For example, when one or more input nodes are mutually connected to one output node by the respective links, the output node may determine an output node value based on values input in the input nodes connected with the output node and the weights set in the links corresponding to the respective input nodes.

As described above, in the neural network, one or more nodes are connected to each other through one or more links to form a relationship of the input node and output node in the neural network. A characteristic of the neural network may be determined according to the number of nodes, the number of links, correlations between the nodes and the links, and values of the weights granted to the respective links in the neural network. For example, when the same number of nodes and links exist and there are two neural networks in which the weight values of the links are different from each other, it may be recognized that two neural networks are different from each other.

The neural network may be configured to include one or more nodes. Some of the nodes constituting the neural network may constitute one layer based on the distances from the initial input node. For example, a set of nodes of which distance from the initial input node is n may constitute n layers. The distance from the initial input node may be defined by the minimum number of links which should be passed through for reaching the corresponding node from the initial input node. However, definition of the layer is predetermined (or selected) for description and the order of the layer in the neural network may be defined by a method different from the aforementioned method. For example, the layers of the nodes may be defined by the distance from a final output node.

The initial input node may mean one or more nodes in which data is directly input without passing through the links in the relationships with other nodes among the nodes in the neural network. Alternatively, in the neural network, in the relationship between the nodes based on the link, the initial input node may mean nodes which other input nodes connected through the links do not have. Similarly thereto, the final output node may mean one or more nodes which do not have the output node in the relationship with other nodes among the nodes in the neural network. Further, a hidden node may mean not the initial input node and the final output node but the nodes constituting the neural network. In the neural network according to an embodiment of the present disclosure, the number of nodes of the input layer may be the same as the number of nodes of the output layer, and the neural network may be a neural network of a type in which the number of nodes decreases and then, increases again from the input layer to the hidden layer. Further, in the neural network according to another embodiment of the present disclosure, the number of nodes of the input layer may be smaller than the number of nodes of the output layer, and the neural network may be a neural network of a type in which the number of nodes decreases from the input layer to the hidden layer. Further, in the neural network according to yet another embodiment of the present disclosure, the number of nodes of the input layer may be larger than the number of nodes of the output layer, and the neural network may be a neural network of a type in which the number of nodes increases from the input layer to the hidden layer. The neural network according to still yet another embodiment of the present disclosure may be a neural network of a type in which the neural networks are combined.

A deep neural network (DNN) may refer to a neural network that includes a plurality of hidden layers in addition to the input and output layers. When the deep neural network is used, the latent structures of data may be determined. That is, potential structures of photos, text, video, voice, and music (e.g., what objects are in the picture, what the content and feelings of the text are, what the content and feelings of the voice are) may be determined. The deep neural network may include a convolutional neural network, a recurrent neural network (RNN), an auto encoder, generative adversarial networks (GAN), a restricted Boltzmann machine (RBM), a deep belief network (DBN), a Q network, a U network, a Siam network, and the like. The description of the deep neural network described above is just an example and the present disclosure is not limited thereto.

In an embodiment of the present disclosure, the network function may include the auto encoder. The auto encoder may be a kind of artificial neural network for outputting output data similar to input data. The auto encoder may include at least one hidden layer and odd hidden layers may be disposed between the input and output layers. The number of nodes in each layer may be reduced from the number of nodes in the input layer to an intermediate layer called a bottleneck layer (encoding), and then expanded symmetrical to reduction to the output layer (symmetrical to the input layer) in the bottleneck layer. In this case, in the example of FIG. 2, it is illustrated that the dimension reduction layer and the dimension reconstruction layer are symmetric, but the present disclosure is not limited thereto and the nodes of the dimension reduction layer and the dimension reconstruction layer may be symmetric or not. The auto encoder may perform non-linear dimensional reduction. The number of input and output layers may correspond to the number of sensors remaining after preprocessing the input data. The auto encoder structure may have a structure in which the number of nodes in the hidden layer included in the encoder decreases as a distance from the input layer increases. When the number of nodes in the bottleneck layer (a layer having a smallest number of nodes positioned between an encoder and a decoder) is too small, a sufficient amount of information may not be delivered, and as a result, the number of nodes in the bottleneck layer may be maintained to be a specific number or more (e.g., half of the input layers or more).

The neural network may be learned in at least one scheme of supervised learning, unsupervised learning, and semi supervised learning. Learning of the neural network is to reduce or minimize errors in output. The learning of the neural network is a process of repeatedly inputting learning data into the neural network and calculating the output of the neural network for the learning data and the error of a target and back-propagating the errors of the neural network from the output layer of the neural network toward the input layer in a direction to reduce the errors to update the weight of each node of the neural network. In the case of the supervised learning, the learning data labeled with a correct answer is used for each learning data (e.g., the labeled learning data) and in the case of the unsupervised learning, the correct answer may not be labeled in each learning data. That is, for example, the learning data in the case of the supervised learning related to the data classification may be data in which category is labeled in each learning data. The labeled learning data is input to the neural network, and the error may be calculated by comparing the output (category) of the neural network with the label of the learning data. As another example, in the case of the unsupervised learning related to the data classification, the learning data as the input is compared with the output of the neural network to calculate the error. The calculated error is back-propagated in a reverse direction (e.g., a direction from the output layer toward the input layer) in the neural network and connection weights of respective nodes of each layer of the neural network may be updated according to the back propagation. A variation amount of the updated connection weight of each node may be determined according to a learning rate. Calculation of the neural network for the input data and the back-propagation of the error may constitute a learning cycle (epoch). The learning rate may be applied differently according to the number of repetition times of the learning cycle of the neural network. For example, in an initial stage of the learning of the neural network, the neural network ensures a certain level of performance quickly by using a high learning rate, thereby increasing efficiency and uses a low learning rate in a latter stage of the learning, thereby increasing accuracy.

In learning of the neural network, the learning data may be generally a subset of actual data (e.g., data to be processed using the learned neural network) of actual data, and as a result, there may be a learning cycle in which errors for the learning data decrease, but the errors for the actual data increase. Overfitting is a phenomenon in which the errors for the actual data increase due to excessive learning of the learning data. For example, a phenomenon in which the neural network that learns a cat by showing a yellow cat sees a cat other than the yellow cat and does not recognize the corresponding cat as the cat may be a kind of overfitting. The overfitting may act as a cause which increases the error of the machine learning algorithm. Various optimization methods may be used in order to prevent the overfitting. In order to prevent the overfitting, a method such as increasing the learning data, regularization, dropout of omitting a part of the node of the network in the process of learning, etc., may be applied.

According to the embodiment of the present disclosure, a computer readable medium storing a data structure is disclosed.

The data structure may refer to organization, management, and storage of data that enable efficient access and modification of data. The data structure may refer to organization of data for solving a specific problem (for example, data search, data storage, and data modification in the shortest time). The data structure may also be defined with a physical or logical relationship between the data elements designed to support a specific data processing function. A logical relationship between data elements may include a connection relationship between user defined data elements. A physical relationship between data elements may include an actual relationship between the data elements physically stored in a computer readable storage medium (for example, a permanent storage device). In particular, the data structure may include a set of data, a relationship between data, and a function or a command applicable to data. Through the effectively designed data structure, the computing device may perform a calculation while minimally using resources of the computing device. In particular, the computing device may improve efficiency of calculation, reading, insertion, deletion, comparison, exchange, and search through the effectively designed data structure.

The data structure may be divided into a linear data structure and a non-linear data structure according to the form of the data structure. The linear data structure may be the structure in which only one data is connected after one data. The linear data structure may include a list, a stack, a queue, and a deque. The list may mean a series of dataset in which order exists internally. The list may include a linked list. The linked list may have a data structure including data connection in which each data has a pointer and is linked in a single line. In the linked list, the pointer may include information about the connection with the next or previous data. The linked list may be expressed as a single linked list, a double linked list, and a circular linked list according to the form. The stack may have a data listing structure with limited access to data. The stack may have a linear data structure that may process (for example, insert or delete) data only at one end of the data structure. The data stored in the stack may have a data structure (Last In First Out, LIFO) in which the later the data enters, the sooner the data comes out. The queue is a data listing structure with limited access to data, and may have a data structure (First In First Out, FIFO) in which the later the data is stored, the later the data comes out, unlike the stack. The deque may have a data structure that may process data at both ends of the data structure.

The non-linear data structure may be the structure in which the plurality of pieces of data is connected after one data. The non-linear data structure may include a graph data structure. The graph data structure may be defined with a vertex and an edge, and the edge may include a line connecting two different vertexes. The graph data structure may include a tree data structure. The tree data structure may be the data structure in which a path connecting two different vertexes among the plurality of vertexes included in the tree is one. That is, the tree data structure may be the data structure in which a loop is not formed in the graph data structure.

Throughout the present specification, a calculation model, a nerve network, the network function, and the neural network may be used with the same meaning. Hereinafter, the terms of the calculation model, the nerve network, the network function, and the neural network are unified and described with a neural network. The data structure may include a neural network. Further, the data structure including the neural network may be stored in a computer readable medium. The data structure including the neural network may also include preprocessed data for processing by the neural network, data input to the neural network, a weight of the neural network, a hyper-parameter of the neural network, data obtained from the neural network, an active function associated with each node or layer of the neural network, and a loss function for training of the neural network. The data structure including the neural network may include predetermined configuration elements among the disclosed configurations. That is, the data structure including the neural network may include the entirety or a predetermined combination of pre-processed data for processing by neural network, data input to the neural network, a weight of the neural network, a hyper parameter of the neural network, data obtained from the neural network, an active function associated with each node or layer of the neural network, and a loss function for training the neural network. In addition to the foregoing configurations, the data structure including the neural network may include predetermined other information determining a characteristic of the neural network. Further, the data structure may include all type of data used or generated in a computation process of the neural network, and is not limited to the foregoing matter. The computer readable medium may include a computer readable recording medium and/or a computer readable transmission medium. The neural network may be formed of a set of interconnected calculation units which are generally referred to as "nodes." The "nodes" may also be called "neurons." The neural network consists of one or more nodes.

The data structure may include data input to the neural network. The data structure including the data input to the neural network may be stored in the computer readable medium. The data input to the neural network may include training data input in the training process of the neural network and/or input data input to the training completed neural network. The data input to the neural network may include data that has undergone pre-processing and/or data to be pre-processed. The pre-processing may include a data processing process for inputting data to the neural network. Accordingly, the data structure may include data to be pre-processed and data generated by the pre-processing. The foregoing data structure is merely an example, and the present disclosure is not limited thereto.

The data structure may include a weight of the neural network. (In the present specification, weights and parameters may be used with the same meaning.) Further, the data structure including the weight of the neural network may be stored in the computer readable medium. The neural network may include a plurality of weights. The weight is variable, and in order for the neural network to perform a desired (or selected) function, the weight may be varied by a user or an algorithm. For example, when one or more input nodes are connected to one output node by links, respectively, the output node may determine a data value output from the output node based on values input to the input nodes connected to the output node and the weight set in the link corresponding to each of the input nodes. The foregoing data structure is merely an example, and the present disclosure is not limited thereto.

For a non-limited example, the weight may include a weight varied in the neural network training process and/or the weight when the training of the neural network is completed. The weight varied in the neural network training process may include a weight at a time at which a training cycle starts and/or a weight varied during a training cycle. The weight when the training of the neural network is completed may include a weight of the neural network completing the training cycle. Accordingly, the data structure including the weight of the neural network may include the data structure including the weight varied in the neural network training process and/or the weight when the training of the neural network is completed. Accordingly, it is assumed that the weight and/or a combination of the respective weights are included in the data structure including the weight of the neural network. The foregoing data structure is merely an example, and the present disclosure is not limited thereto.

The data structure including the weight of the neural network may be stored in the computer readable storage medium (for example, a memory and a hard disk) after undergoing a serialization process. The serialization may be the process of storing the data structure in the same or different computing devices and converting the data structure into a form that may be reconstructed and used later. The computing device may serialize the data structure and transceive the data through a network. The serialized data structure including the weight of the neural network may be reconstructed in the same or different computing devices through deserialization. The data structure including the weight of the neural network is not limited to the serialization. Further, the data structure including the weight of the neural network may include a data structure (for example, in the non-linear data structure, B-Tree, Trie, m-way search tree, AVL tree, and Red-Black Tree) for improving efficiency of the calculation while minimally using the resources of the computing device. The foregoing matter is merely an example, and the present disclosure is not limited thereto.

The data structure may include a hyper-parameter of the neural network. The data structure including the hyper-parameter of the neural network may be stored in the computer readable medium. The hyper-parameter may be a variable varied by a user. The hyper-parameter may include, for example, a learning rate, a cost function, the number of times of repetition of the training cycle, weight initialization (for example, setting of a range of a weight value to be weight-initialized), and the number of hidden units (for example, the number of hidden layers and the number of nodes of the hidden layer). The foregoing data structure is merely an example, and the present disclosure is not limited thereto.

According to the embodiment of the present disclosure, there are multiple anatomical analysis models 212, and the anatomical analysis models 212 may be the trained neural network models configured with different algorithms, or may be configured with one or more subset models. The trained neural network model may be a Convolutional Neural Network (CNN), and the CNN is a sort of a deep neural network and includes a neural network including a convolutional layer. The CNN is a type of multilayer perceptrons specialized for image processing. The CNN may consist of one or more several convolutional layers and artificial neural network layers combined with the convolutional layers. The CNN may additionally use a weight and pooling layers. Due to the structure, the CNN may sufficiently use input data of a two-dimensional structure. The convolutional neural network may be used to recognize an object in an image. The convolutional neural network may represent and process image data with a matrix having a dimension. For example, in the case of image data encoded in red-green-blue (RGB), each R, G, and B color may be represented as two-dimensional (for example, in the case of a two-dimensional image) matrix. That is, a color value of each pixel of the image data may be a component of the matrix, and a size of the matrix may be the same as the size of the image. Accordingly, the image data may be represented with three two-dimensional matrixes (a three-dimensional data array).

A convolutional process (input/output of the convolutional layer) may be performed by multiplying a convolutional filter and a component of the matrix in each position of the image while moving the convolutional filter in the convolutional neural network. The convolutional filter may be formed of an n×n matrix. The convolutional filter may be generally formed of the fixed type of filter of which the number of pixels is generally smaller than the total number of pixels of the image. That is, in the case where an m×m image is input to the convolutional layer (for example, a convolutional layer in which a size of the convolutional filter is n×n), the matrix representing n×n pixels including each pixel of the image may be a multiplication of the convolutional filter and the component (that is, the multiplication of each component of the matrix). By the multiplication of the convolutional filter and the component, the component matching the convolutional filter may be extracted from the image. For example, a 3×3 convolutional filter for extracting upper and lower linear components from an image may be configured as [[0,1,0], [0,1,0], [0,1,0]]. When the 3×3 convolutional filter for extracting the upper and lower linear components from the image is applied to the input image, the upper and lower linear components matching the convolutional filter are extracted from the image and output. The convolutional layer may apply the convolutional filter to each matrix (that is, in the case of R, G, B coding image, R, G, and B colors) for each channel representing the image. The convolutional layer may extract a feature matching the convolutional filter from the input image by applying the convolutional filter to the input image. The filter value (that is, the value of each component of the matrix) of the convolutional filter may be updated by backpropagation in the training process of the convolutional neural network.

A sub-sampling layer is connected to the output of the convolutional layer to simplify the output of the convolutional layer and reduce the amount of use of the memory and the amount of computation. For example, when the output of the convolutional layer is input to the pooling layer having a 2×2 max pooling filter, the image may be compressed by outputting the maximum value included in each patch for each 2×2 patch in each pixel of the image. The foregoing pooling may also be the scheme of outputting a minimum value in the patch or outputting an average value of the patch, and a predetermined pooling scheme may be included in the present disclosure.

The convolutional neural network may include one or more convolutional layers and a sub-sampling layer. The convolutional neural network may extract a feature from an image by repeatedly performing a convolutional process and a sub-sampling process (for example, the foregoing max pooling and the like). Through the repeated convolutional process and the sub-sampling process, the neural network may extract a global feature from the image.

The output of the convolutional layer or the sub-sampling layer may be input to a fully connected layer. The fully connected layer is the layer in which all of the neurons in one layer are connected to all of the neurons in an adjacent layer. The fully connected layer may mean a structure in which all of the nodes of each layer are connected to all of the nodes of another layer in the neural network.

In the embodiment of the present disclosure, in order to extract a body region having an anatomical significance from a body medical image, the anatomical analysis model 212 may be used.

The anatomical analysis model 212 may also be the same model as the foregoing pre-trained neural network model or may be a different model from the foregoing pre-trained neural network model.

In the embodiment of the present disclosure, the processor 120 may generate a diagnosis result for the received body medical image based on the anatomical location information about the one or more detected lesions. In particular, the processor 120 may generate clinical information representing a clinical significance in a situation where the one or more detected lesions are related to the anatomical location information. The clinical information may include an occurrence frequency of lesion for each of the regions divided from the body region, which is extracted from the received body medical image and has the anatomical significance and a degree of risk of lesion for each of the divided regions. In particular, a lesion that is difficult to be located in a specific region may exist, and conversely, a lesion with a high probability of occurring in a specific region may exist. Further, the existence of a specific lesion in a specific region may be dangerous. For example, when a specific lesion occurs in the airway region extracted from the cervical X-ray image, the degree of risk may be higher in the airway region, compared to other regions. The example of the degree of risk of lesion is illustrative, and the present disclosure is not limited thereto.

In the embodiment of the present disclosure, the processor 120 may change a confidence score, which has been determined in the operation of detecting the one or more detected lesions, based on the occurrence frequency of the lesion for each of the divided regions obtained from clinical statistical information. In particular, when a lesion that is difficult to be located in a specific region is detected in the corresponding specific region, the processor 120 may make a correction to reduce the confidence score of the detected lesion. Otherwise, when a lesion with a high probability of occurring in a specific region is detected in the corresponding specific region, the processor 120 may make a correction to increase the confidence score of the detected lesion. For example, when a nodule is detected in the upper lobe of the left lung and the confidence score is calculated as 40%, the processor 120 may change the confidence score for the corresponding nodule from 40% to 60%. The example of the change in the confidence score is merely illustrative, and the present disclosure is not limited thereto.

The processor 120 may generate clinical information about the one or more detected lesions based on the degree of risk for the lesion for each of the divided region and the changed confidence score obtained from the clinical statistical information. In particular, when the detected lesion exists in the specific region in which the corresponding lesion is detected and is danger, the processor 120 may display a notification for the corresponding lesion and generate a diagnosis result. For example, in the case where a nodule is detected in the airway region of the cervical X-ray image, when the processor 120 generates the diagnosis result including a notification for the corresponding nodule, the processor 120 may generate a notification in the form of an exclamation mark (!), "danger" or a highlight color and display the diagnosis result. The example of the notification is merely illustrative, and the present disclosure is not limited thereto.

In the embodiment of the present disclosure, the user interface may include a notification area for providing additional information according to the degree of risk of the detected lesion, and whether to display the notification area may be determined based on at least one of the anatomical location information, the clinical information, and the confidence score of the one or more lesions.

The processor 120 according to the embodiment of the present disclosure may provide the user interface in which the degree of sensitiveness for the notification is adjusted according to user's setting or the confidence score. For example, when it is detected that the lesion that is difficult to be located in the upper left part of the lung exists, the user interface may display the notification to the user only when the confidence score is higher than a first threshold. For another example, when a lesion existing at a specific location has high clinical significance (for example, a lesion that blocks the airway has higher severity than a lesion at another location), the user interface may display the notification to the user even though the confidence score is lower than the first threshold.

In the embodiment of the present disclosure, the processor 120 may generate a readout through the readout generation model 222 based on the generated clinical information. In particular, the processor 120 may input the clinical information to the readout generation model 222 of the diagnosis result generation unit 220 and generate a readout in the form of a sentence as an output value. For example, the processor 120 may generate a readout, such as "a nodule is spread in the middle lobe of the left lung of the lung region, and there is a high possibility in that the nodule is spread to the upper lobe and the lower lobes, which is dangerous," based on the clinical information that the plurality of nodules is detected for the lung region, the confidence score is 80%, and the nodules are spread in the middle lobe of the left lung, and the degree of risk is high by using the readout generation model 222. Otherwise, the processor 120 may generate a readout, such as "it is suspected that the nodule exists in the bronchial tubes in the airway area. The size of the nodule is above an average, so that the bronchial tubes may be narrowed, and there is a possibility of breathing problems, which is very dangerous," based on the clinical information, such as the fact that the nodule is detected in the bronchial tubes of the airway area, the fact that the confidence score is 50%, the size of the nodule (a diameter is about 7 mm), and the fact that the degree of risk is very high, by using the readout generation model 222. The example of the readout is merely illustrative, and the present disclosure is not limited thereto. Further, the readout generation model according to the embodiment of the present disclosure is the model performing predetermined natural language processing, and may be performed through a predetermined morpheme analysis algorithm or may be a deep learning-based model.

In the embodiment of the present disclosure, the processor 120 may correct the generated readout by reflecting a correction input of a user. A corrected diagnosis result including the corrected readout may be displayed on the user interface. In the embodiment, the readout for the body medical image is generated based on the deep learning technology, and the user reviews the generated readout, so that a final diagnosis result to which the correction content is reflected may be generated.

In the embodiment of the present disclosure, the server may transmit the readout or the diagnosis result generated by the foregoing method to the terminal. In this case, the terminal may output the generated readout or diagnosis result while interacting with the user through the user interface.

In another embodiment of the present disclosure, the readout or the diagnosis result generated by the foregoing method may be generated in the terminal and output through the user interface of the terminal.

In another embodiment of the present disclosure, some steps in the operation of generating the readout or the diagnosis result are performed by the server and the remaining steps are performed by the terminal, so that the terminal may also finally generate the readout or the diagnosis result. FIG. 5 is a diagram illustrating a user interface according to the embodiment of the present disclosure.

In the embodiment of the present disclosure, the processor 120 may generate a user interface (UI) displaying information about the diagnosis result. The user interface may be generated by the server or the terminal and provided to the user by the terminal.

In particular, the processor 120 may generate the diagnosis result through the diagnosis result generation unit 220. The processor 120 may generate a user interface for displaying information about the generated diagnosis result, and herein, the user interface may include a first area 510 for displaying the one or more lesions detected from the received body medical image, a second area 520 for displaying summary information about the one or more detected lesions, and a third area 530 for displaying a readout corresponding to the diagnosis result.

In the embodiment, the first area 510, the second area 520, and the third area 530 may form the independent areas in one layer. In another embodiment, each of the first area 510, the second area 520, and the third area 530 may form one layer, and overlap each other according to a user's input. In another embodiment, at least two of the first area 510, the second area 520, and the third area 530 may be combined with each other and displayed as one combined area.

In particular, the first region for displaying the body medical image including the information about the one or more detected lesions may be the area for displaying the location of the detected lesion in the body medical image and displaying a distribution region based on the distribution of the lesion. Further, the second area for displaying the summary information about the one or more detected lesions may be a screen which intuitively summarizes and displays the findings (for example, the type and size of the lesion) or the location of the detected lesion, or the confidence score for the existence of the lesion. Further, the third area for displaying the readout may display a readout generated in the form of a sentence based on the summary information about the one or more detected lesions. For example, the readout, such as "it is suspected that the nodule exists in the bronchial tubes in the airway area. The size of the nodule is above an average, so that the bronchial tubes may be narrowed, and there is a possibility of breathing problems, which is very dangerous," may be displayed.

In the embodiment of the present disclosure, the user interface may further include a notification area for providing additional information according to the degree of risk of the detected lesion, and whether to display the notification area is determined based on at least one of the anatomical location information, the clinical information, and the confidence score of the one or more lesions. For example, by the anatomical location information or the clinical information, in the case of a lesion existing in a specific location (dangerous location), even though the confidence score is low, the notification area may be activated, and conversely, in the case of a lesion existing in a specific location (not-dangerous location), only when the confidence score is high, the notification area may be activated.

According to the embodiment of the present disclosure, the user interface may display a corrected diagnosis result in response to the detection of a user input interacting with the user interface.

Figure 6:
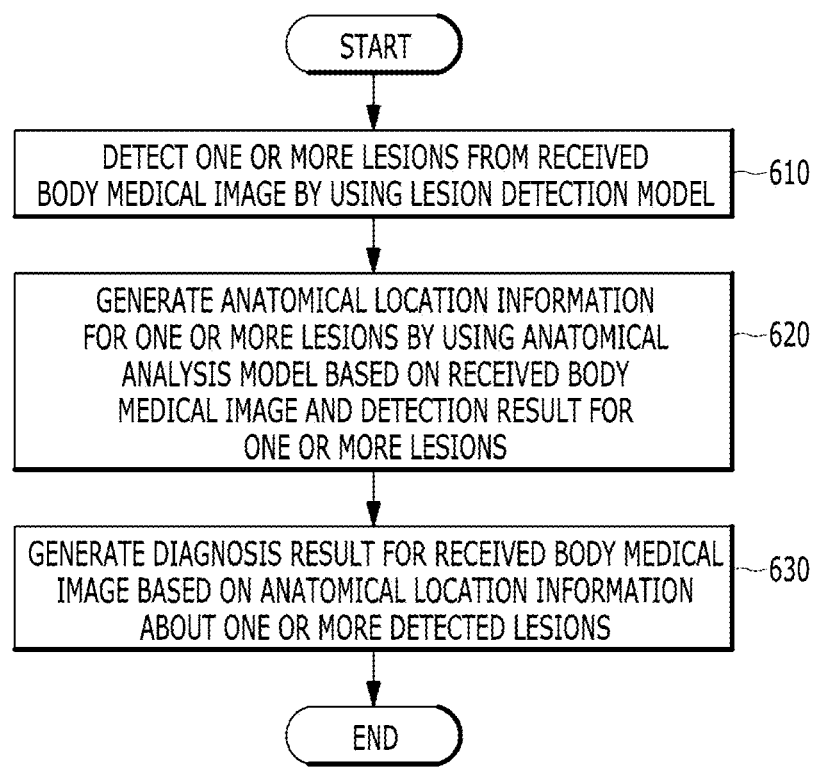
FIG. 6 is a flowchart illustrating a method of generating a diagnosis result for a body medical image according to an embodiment of the present disclosure.

FIG. 6 is a flowchart illustrating a method of generating a diagnosis result for a body medical image according to an embodiment of the present disclosure.

The computing device 100 may receive a body medical image. The computing device 100 may detect one or more lesions from the received body medical image by using the lesion detection model (610). The computing device 100 may determine type information of the one or more lesions included in the received body medical image. The computing device 100 may determine a confidence score corresponding to the determined type information of the one or more lesions. Further, the computing device 100 may generate outline information of the one or more determined lesions.

The computing device 100 may generate anatomical location information for the one or more lesions by using an anatomical analysis model based on the received body medical image and a detection result for the one or more lesions (620). The computing device 100 may generate anatomical location information indicating that one or more lesions exist at the determined location.

The computing device 100 may generate a diagnosis result for the received body medical image based on the anatomical location information about the one or more lesions (630). The computing device 100 may generate clinical information representing a clinical significance in a situation where the one or more detected lesions are related to the anatomical location information. The computing device 100 may generate a readout by using the readout generation model based on the generated clinical information. The clinical information may include an occurrence frequency of lesion for each of the regions divided from the body region, which is extracted from the received body medical image and has the anatomical significance and a degree of risk of lesion for each of the divided regions. Further, the computing device 100 may change a confidence score, which has been determined in the operation of detecting the one or more detected lesions, based on the occurrence frequency of the lesion for each of the divided regions obtained from clinical statistical information. The computing device 100 may generate the clinical information based on the degree of danger in the situation where the lesion exists in each of the divided regions and the changed confidence score obtained from the clinical statistical information.

The computing device 100 may generate a readout by using the readout generation model based on the generated clinical information. The computing device 100 may generate a diagnosis result for the received body medical image based on the generated readout.

The computing device 100 may generate a user interface (UI) displaying information about the diagnosis result. The user interface may include a first area for displaying the one or more lesions detected from the received body medical image, a second area for displaying summary information about the one or more detected lesions, and a third area for displaying a readout corresponding to the diagnosis result.

Figure 7:
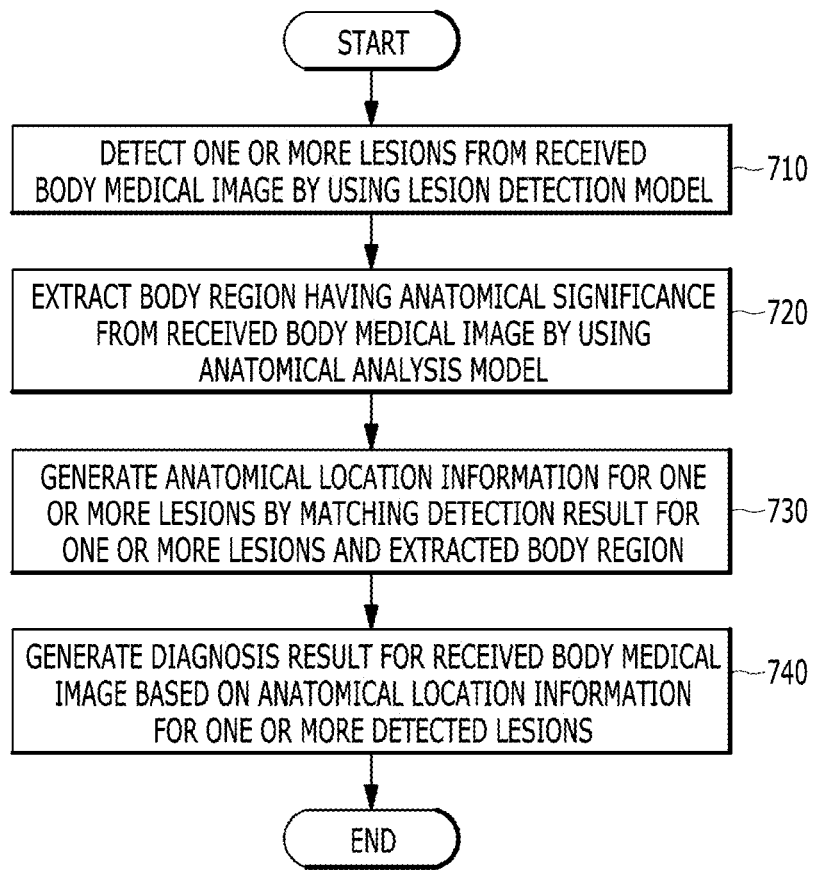
FIG. 7 is a flowchart illustrating a method of generating a diagnosis result for a body medical image according to an embodiment of the present disclosure.

FIG. 7 is a flowchart illustrating a method of generating a diagnosis result for a body medical image according to an embodiment of the present disclosure.

The computing device 100 may receive a body medical image. The computing device 100 may detect one or more lesions from the received body medical image by using the lesion detection model (710). The computing device 100 may determine type information of the one or more lesions included in the received body medical image. Further, the computing device 100 may determine a confidence score corresponding to the determined type information of the one or more lesions. The computing device 100 may generate outline information of the one or more determined lesions.

The computing device 100 may extract a body region having an anatomical significance from the received body medical image by using the anatomical analysis model.

The computing device 100 may generate anatomical location information for the one or more lesions by matching a detection result for the one or more detected lesions and the extracted body region (730). The extracted body region may be divided into a plurality of sub regions. The computing device 100 may determine a location, at which the one or more lesions exist, in the divided sub regions by matching the detection result for the one or more detected lesions and the plurality of sub regions for the extracted body region. Further, the computing device 100 may generate anatomical location information indicating that one or more lesions exist at the determined location.

The computing device 100 may generate a diagnosis result for the received body medical image based on the anatomical location information about the one or more lesions (740). The computing device 100 may generate clinical information representing a clinical significance in a situation where the one or more detected lesions are related to the anatomical location information. The computing device 100 may generate a readout by using the readout generation model based on the generated clinical information. The clinical information may include an occurrence frequency of lesion for each of the regions divided from the body region, which is extracted from the received body medical image and has the anatomical significance and a degree of risk of lesion for each of the divided regions. Further, the computing device 100 may change a confidence score, which has been determined in the operation of detecting the one or more lesions, based on the occurrence frequency of the lesion for each of the divided regions obtained from clinical statistical information. The computing device 100 may generate the clinical information based on the degree of danger in the situation where the lesion exists in each of the divided regions and the changed confidence score obtained from the clinical statistical information.

The computing device 100 may generate a readout by using the readout generation model based on the generated clinical information. The computing device 100 may correct the readout according to a correction input of a user. The computing device 100 may generate a diagnosis result for the received body medical image based on the generated or corrected readout.

In the embodiment of the present disclosure, the computing device 100 may transmit the generated readout or diagnosis result to a terminal. In this case, the terminal may interact with the user by outputting the generated readout or diagnosis result on a user interface.

In another embodiment of the present disclosure, the computing device 100 may generate the generated readout or diagnosis result and output the generated readout or diagnosis result through the user interface.

In another embodiment of the present disclosure, some steps in the operation of generating the readout or the diagnosis result may be performed by the server and the remaining steps may be performed by the terminal.

The computing device 100 may generate a user interface (UI) displaying information about the diagnosis result. The user interface may include a first area for displaying the one or more lesions detected from the received body medical image, a second area for displaying summary information about the one or more detected lesions, and a third area for displaying a readout corresponding to the diagnosis result.

Figure 8:
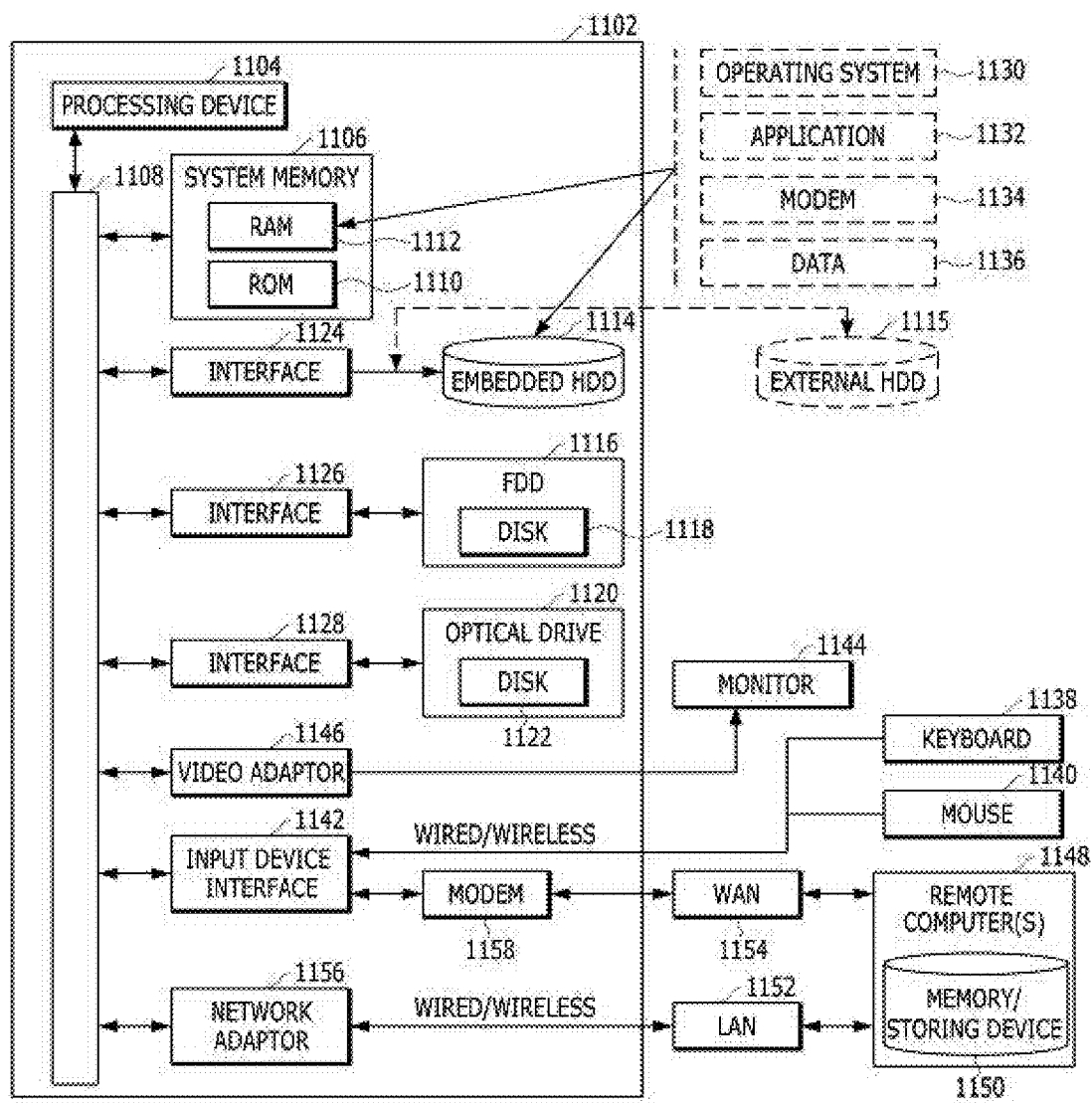
FIG. 8 is a block diagram illustrating a computing device according to an embodiment of the present disclosure.

FIG. 8 is a simple and normal schematic view of a computing environment in which the embodiments of the present disclosure may be implemented.

It is described above that the present disclosure may be generally implemented by the computing device, but those skilled in the art will well know that the present disclosure may be implemented in association with a computer executable command which may be executed on one or more computers and/or in combination with other program modules and/or as a combination of hardware and software.

In general, the program module includes a routine, a program, a component, a data structure, and the like that execute a specific task or implement a specific abstract data type. Further, it will be well appreciated by those skilled in the art that the method of the present disclosure can be implemented by other computer system configurations including a personal computer, a handheld computing device, microprocessor-based or programmable home appliances, and others (the respective devices may operate in connection with one or more associated devices as well as a single-processor or multi-processor computer system, a mini computer, and a main frame computer.

The embodiments described in the present disclosure may also be implemented in a distributed computing environment in which predetermined (or selected) tasks are performed by remote processing devices connected through a communication network. In the distributed computing environment, the program module may be positioned in both local and remote memory storage devices.

The computer generally includes various computer readable media. Media accessible by the computer may be computer readable media regardless of types thereof and the computer readable media include volatile and non-volatile media, transitory and non-transitory media, and mobile and non-mobile media. As a non-limiting example, the computer readable media may include both computer readable storage media and computer readable transmission media. The computer readable storage media include volatile and non-volatile media, temporary and non-temporary media, and movable and non-movable media implemented by a predetermined (or selected) method or technology for storing information such as a computer readable instruction, a data structure, a program module, or other data. The computer readable storage media include a RAM, a ROM, an EEPROM, a flash memory or other memory technologies, a CD-ROM, a digital video disk (DVD) or other optical disk storage devices, a magnetic cassette, a magnetic tape, a magnetic disk storage device or other magnetic storage devices or predetermined (or selected) other media which may be accessed by the computer or may be used to store desired (or selected) information, but are not limited thereto.

The computer readable transmission media generally implement the computer readable command, the data structure, the program module, or other data in a carrier wave or a modulated data signal such as other transport mechanism and include all information transfer media. The term "modulated data signal" means a signal acquired by configuring or changing at least one of characteristics of the signal so as to encode information in the signal. As a non-limiting example, the computer readable transmission media include wired media such as a wired network or a direct-wired connection and wireless media such as acoustic, RF, infrared and other wireless media. A combination of any media among the aforementioned media is also included in a range of the computer readable transmission media.

An environment 1100 that implements various aspects of the present disclosure including a computer 1102 is shown and the computer 1102 includes a processing device 1104, a system memory 1106, and a system bus 1108. The system bus 1108 connects system components including the system memory 1106 (not limited thereto) to the processing device 1104. The processing device 1104 may be a predetermined (or selected) processor among various commercial processors. A dual processor and other multi-processor architectures may also be used as the processing device 1104.

The system bus 1108 may be any one of several types of bus structures which may be additionally interconnected to a local bus using any one of a memory bus, a peripheral device bus, and various commercial bus architectures. The system memory 1106 includes a read only memory (ROM) 1110 and a random access memory (RAM) 1112. A basic input/output system (BIOS) is stored in the non-volatile memories 1110 including the ROM, the EPROM, the EEPROM, and the like and the BIOS includes a basic routine that assists in transmitting information among components in the computer 1102 at a time such as in-starting.

The RAM 1112 may also include a high-speed RAM including a static RAM for caching data, and the like.

The computer 1102 also includes an interior hard disk drive (HDD) 1114 (for example, EIDE and SATA), in which the interior hard disk drive 1114 may also be configured for an exterior purpose in an appropriate chassis (not illustrated), a magnetic floppy disk drive (FDD) 1116 (for example, for reading from or writing in a mobile diskette 1118), and an optical disk drive 1120 (for example, for reading a CD-ROM disk 1122 or reading from or writing in other high-capacity optical media such as the DVD, and the like). The hard disk drive 1114, the magnetic disk drive 1116, and the optical disk drive 1120 may be connected to the system bus 1108 by a hard disk drive interface 1124, a magnetic disk drive interface 1126, and an optical drive interface 1128, respectively. An interface 1124 for implementing an exterior drive includes at least one of a universal serial bus (USB) and an IEEE 1394 interface technology or both of them.

The drives and the computer readable media associated therewith provide non-volatile storage of the data, the data structure, the computer executable instruction, and others. In the case of the computer 1102, the drives and the media correspond to storing of predetermined (or selected) data in an appropriate digital format. In the description of the computer readable media, the mobile optical media such as the HDD, the mobile magnetic disk, and the CD or the DVD are mentioned, but it will be well appreciated by those skilled in the art that other types of media readable by the computer such as a zip drive, a magnetic cassette, a flash memory card, a cartridge, and others may also be used in an operating environment and further, the predetermined (or selected) media may include computer executable commands for executing the methods of the present disclosure.

Multiple program modules including an operating system 1130, one or more application programs 1132, other program module 1134, and program data 1136 may be stored in the drive and the RAM 1112. All or some of the operating system, the application, the module, and/or the data may also be cached in the RAM 1112. It will be well appreciated that the present disclosure may be implemented in operating systems which are commercially usable or a combination of the operating systems.

A user may input instructions and information in the computer 1102 through one or more wired/wireless input devices, for example, pointing devices such as a keyboard 1138 and a mouse 1140. Other input devices (not illustrated) may include a microphone, an IR remote controller, a joystick, a game pad, a stylus pen, a touch screen, and others. These and other input devices are often connected to the processing device 1104 through an input device interface 1142 connected to the system bus 1108, but may be connected by other interfaces including a parallel port, an IEEE 1394 serial port, a game port, a USB port, an IR interface, and others.

A monitor 1144 or other types of display devices are also connected to the system bus 1108 through interfaces such as a video adapter 1146, and the like. In addition to the monitor 1144, the computer generally includes other peripheral output devices (not illustrated) such as a speaker, a printer, others.

The computer 1102 may operate in a networked environment by using a logical connection to one or more remote computers including remote computer(s) 1148 through wired and/or wireless communication. The remote computer(s) 1148 may be a workstation, a computing device computer, a router, a personal computer, a portable computer, a micro-processor based entertainment apparatus, a peer device, or other general network nodes and generally includes multiple components or all of the components described with respect to the computer 1102, but only a memory storage device 1150 is illustrated for brief description. The illustrated logical connection includes a wired/wireless connection to a local area network (LAN) 1152 and/or a larger network, for example, a wide area network (WAN) 1154. The LAN and WAN networking environments are general environments in offices and companies and facilitate an enterprise-wide computer network such as Intranet, and all of them may be connected to a worldwide computer network, for example, the Internet.

When the computer 1102 is used in the LAN networking environment, the computer 1102 is connected to a local network 1152 through a wired and/or wireless communication network interface or an adapter 1156. The adapter 1156 may facilitate the wired or wireless communication to the LAN 1152 and the LAN 1152 also includes a wireless access point installed therein in order to communicate with the wireless adapter 1156. When the computer 1102 is used in the WAN networking environment, the computer 1102 may include a modem 1158 or has other means that configure communication through the WAN 1154 such as connection to a communication computing device on the WAN 1154 or connection through the Internet. The modem 1158 which may be an internal or external and wired or wireless device is connected to the system bus 1108 through the serial port interface 1142. In the networked environment, the program modules described with respect to the computer 1102 or some thereof may be stored in the remote memory/storage device 1150. It will be well known that an illustrated network connection is and other means configuring a communication link among computers may be used.

The computer 1102 performs an operation of communicating with predetermined (or selected) wireless devices or entities which are disposed and operated by the wireless communication, for example, the printer, a scanner, a desktop and/or a portable computer, a portable data assistant (PDA), a communication satellite, predetermined (or selected) equipment or place associated with a wireless detectable tag, and a telephone. This at least includes wireless fidelity (Wi-Fi) and Bluetooth wireless technology. Accordingly, communication may be a predefined structure like the network in the related art or just ad hoc communication between at least two devices.

The wireless fidelity (Wi-Fi) enables connection to the Internet, and the like without a wired cable. The Wi-Fi is a wireless technology such as the device, for example, a cellular phone which enables the computer to transmit and receive data indoors or outdoors, that is, anywhere in a communication range of a base station. The Wi-Fi network uses a wireless technology called IEEE 802.11(a, b, g, and others) in order to provide safe, reliable, and high-speed wireless connection. The Wi-Fi may be used to connect the computers to each other or the Internet and the wired network (using IEEE 802.3 or Ethernet). The Wi-Fi network may operate, for example, at a data rate of 11 Mbps (802.11a) or 54 Mbps (802.11b) in unlicensed 2.4 and 5 GHz wireless bands or operate in a product including both bands (dual bands).

It will be appreciated by those skilled in the art that information and signals may be expressed by using various different predetermined (or selected) technologies and techniques. For example, data, instructions, commands, information, signals, bits, symbols, and chips which may be referred in the above description may be expressed by voltages, currents, electromagnetic waves, magnetic fields or particles, optical fields or particles, or predetermined (or selected) combinations thereof.

It may be appreciated by those skilled in the art that various logical blocks, modules, processors, means, circuits, and algorithm steps described in association with the embodiments disclosed herein may be implemented by electronic hardware, various types of programs or design codes (for easy description, herein, designated as software), or a combination of all of them. In order to clearly describe the intercompatibility of the hardware and the software, various components, blocks, modules, circuits, and steps have been generally described above in association with functions thereof. Whether the functions are implemented as the hardware or software depends on design restrictions given to a specific application and an entire system. Those skilled in the art of the present disclosure may implement functions described by various methods with respect to each specific application, but it should not be interpreted that the implementation determination departs from the scope of the present disclosure.

Various embodiments presented herein may be implemented as manufactured articles using a method, an apparatus, or a standard programming and/or engineering technique. The term manufactured article includes a computer program, a carrier, or a medium which is accessible by a predetermined (or selected) computer-readable storage device. For example, a computer-readable storage medium includes a magnetic storage device (for example, a hard disk, a floppy disk, a magnetic strip, or the like), an optical disk (for example, a CD, a DVD, or the like), a smart card, and a flash memory device (for example, an EEPROM, a card, a stick, a key drive, or the like), but is not limited thereto. Further, various storage media presented herein include one or more devices and/or other machine-readable media for storing information.

It will be appreciated that a specific order or a hierarchical structure of steps in the presented processes is one example of accesses. It will be appreciated that the specific order or the hierarchical structure of the steps in the processes within the scope of the present disclosure may be rearranged based on design priorities. Appended method claims provide elements of various steps in a sample order, but the method claims are not limited to the presented specific order or hierarchical structure.

The description of the presented embodiments is provided so that those skilled in the art of the present disclosure use or implement the present disclosure. Various modifications of the embodiments will be apparent to those skilled in the art and general principles defined herein can be applied to other embodiments without departing from the scope of the present disclosure. Therefore, the present disclosure is not limited to the embodiments presented herein, but should be interpreted within the widest range which is coherent with the principles and new features presented herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method performed on one or more processors of a computing device, the method comprising:
receiving a body medical image;
detecting one or more lesions from the received body medical image using a lesion detection model;
extracting a body region having anatomical significance from the received body medical image using an anatomical analysis model;
generating anatomical location information for the one or more lesions by matching the detection result for the one or more lesions with the extracted body region; and
generating a diagnosis result for the received body medical image, based on the anatomical location information for the one or more lesions,
wherein the body region having the anatomical significance is a body organ that is likely to be a point of occurrence of the one or more lesions or a body organ that is a target of the detection of the one or more lesions, and
wherein the generating the diagnosis result for the received body medical image, based on the anatomical location information for the one or more lesions comprising:
generating clinical information indicating clinical significance in a situation in which the one or more lesions are related to the anatomical location information,
wherein the clinical information comprising:
an occurrence frequency of lesion for each of regions divided from the body region having the anatomical significance; and
a degree of risk of lesion for each of the divided regions,
wherein the generating the clinical information indicating the clinical significance in the situation in which the one or more lesions are related to the anatomical location information comprising:
changing a confidence score determined in the step of detecting the one or more lesions, based on the occurrence frequency of lesion for each of the divided regions which is obtained from clinical statistical information; and
generating the clinical information, based on the changed confidence score and based on the degree of risk of lesion for each of the divided regions which is obtained from the clinical statistical information.

2. The method of claim 1, wherein the detecting the one or more lesions from the received body medical image using the lesion detection model comprising:
determining type information of the one or more lesions included in the received body medical image;
determining a confidence score corresponding to the determined type information of the one or more lesions; and
generating contour information of the detected one or more lesions.

3. The method of claim 1, wherein the generating the diagnosis result for the received body medical image, based on the anatomical location information for the one or more lesions further comprising:
generating a readout using a readout generation model, based on the generated clinical information.

4. The method of claim 3, wherein the generating the diagnosis result for the received body medical image, based on the anatomical location information for the one or more lesions further comprising:
modifying the generated readout by reflecting a modification input of a user; and
generating the diagnosis result for the received body medical image based on the modified readout.

5. The method of claim 1, wherein the method further comprising:
generating a user interface including information on the diagnosis result, and
wherein the user interface comprising:
a first area for displaying the detected one or more lesions on the received body medical image;
a second area for displaying summary information about the detected one or more lesions; and
a third area for displaying a readout corresponding to the diagnosis result.

6. The method of claim 5, wherein the user interface further comprising:
a notification area for providing additional information according to a degree of risk of lesion, and
wherein whether to display the notification area is determined based on at least one of the anatomical location information for the one or more lesions or a confidence score for the one or more lesions.

7. The method of claim 1, wherein the extracted body region is divided into a plurality of sub regions, and
wherein the generating the anatomical location information for the one or more lesions comprising:
determining a location in which the one or more lesions exist in the divided sub regions by matching the detection result for the one or more lesions with the plurality of sub regions for the extracted body region; and
generating the anatomical location information indicating that the one or more lesions exist in the determined location.

8. A computer program comprising instructions stored in a non-transitory computer-readable storage medium to cause a computer to perform the following operations, the operations comprising:
receiving a body medical image;
detecting one or more lesions from the received body medical image using a lesion detection model;
extracting a body region having anatomical significance from the received body medical image using an anatomical analysis model;
generating anatomical location information for the one or more lesions by matching the detection result for the one or more lesions with the extracted body region; and
generating a diagnosis result for the received body medical image, based on the anatomical location information for the one or more lesions,
wherein the body region having the anatomical significance is a body organ that is likely to be a point of occurrence of the one or more lesions or a body organ that is a target of the detection of the one or more lesions, and
wherein the generating the diagnosis result for the received body medical image, based on the anatomical location information for the one or more lesions comprising:
generating clinical information indicating clinical significance in a situation in which the one or more lesions are related to the anatomical location information, wherein the clinical information comprising:
an occurrence frequency of lesion for each of regions divided from the body region having the anatomical significance; and
a degree of risk of lesion for each of the divided regions,
wherein the generating the clinical information indicating the clinical significance in the situation in which the one or more lesions are related to the anatomical location information comprising:
changing a confidence score determined in the step of detecting the one or more lesions, based on the occurrence frequency of lesion for each of the divided regions which is obtained from clinical statistical information; and
generating the clinical information, based on the changed confidence score and based on the degree of risk of lesion for each of the divided regions which is obtained from the clinical statistical information.

9. A server, comprising:
a processor including one or more cores;
a network unit for receiving a body medical image; and
a memory,
wherein the processor is configured to:
detect one or more lesions from the received body medical image using a lesion detection model;
extract a body region having anatomical significance from the received body medical image using an anatomical analysis model;
generate anatomical location information for the one or more lesions by matching the detection result for the one or more lesions with the extracted body region; and
generate a diagnosis result for the received body medical image, based on the anatomical location information for the one or more lesions,
wherein the body region having the anatomical significance is a body organ that is likely to be a point of occurrence of the one or more lesions or a body organ that is a target of the detection of the one or more lesions, and
wherein the generating the diagnosis result for the received body medical image, based on the anatomical location information for the one or more lesions comprising:
generating clinical information indicating clinical significance in a situation in which the one or more lesions are related to the anatomical location information,
wherein the clinical information comprising:
an occurrence frequency of lesion for each of regions divided from the body region having the anatomical significance; and
a degree of risk of lesion for each of the divided regions,
wherein the generating the clinical information indicating the clinical significance in the situation in which the one or more lesions are related to the anatomical location information comprising:
changing a confidence score determined in the step of detecting the one or more lesions, based on the occurrence frequency of lesion for each of the divided regions which is obtained from clinical statistical information; and
generating the clinical information, based on the changed confidence score and based on the degree of risk of lesion for each of the divided regions which is obtained from the clinical statistical information.

10. The server of claim 9, wherein the detecting the one or more lesions from the received body medical image using the lesion detection model comprising:
determining type information of the one or more lesions included in the received body medical image;
determining a confidence score corresponding to the determined type information of the one or more lesions; and
generating contour information of the detected one or more lesions.

11. The method of claim 1, wherein the generating the diagnosis result for the received body medical image, based on the anatomical location information for the one or more lesions further comprising: generating a readout using a readout generation model, based on the generated clinical information.

12. The method of claim 11, wherein the generating the diagnosis result for the received body medical image, based on the anatomical location information for the one or more lesions further comprising:
modifying the generated readout by reflecting a modification input of a user; and
generating the diagnosis result for the received body medical image based on the modified readout.

13. The server of claim 9, wherein the processor is further configured to:
generate a user interface including information on the diagnosis result, and
wherein the user interface comprising:
a first area for displaying the detected one or more lesions on the received body medical image;
a second area for displaying summary information about the detected one or more lesions; and
a third area for displaying a readout corresponding to the diagnosis result.

14. The server of claim 13, wherein the user interface further comprising:
a notification area for providing additional information according to a degree of risk of lesion, and
wherein whether to display the notification area is determined based on at least one of the anatomical location information for the one or more lesions or a confidence score for the one or more lesions.

15. The server of claim 9, wherein the extracted body region is divided into a plurality of sub regions, and
wherein the generating the anatomical location information for the one or more lesions comprising:
determining a location in which the one or more lesions exist in the divided sub regions by matching the detection result for the one or more lesions with the plurality of sub regions for the extracted body region; and
generating the anatomical location information indicating that the one or more lesions exist in the determined location.

* * * * *